United States Patent
Kitaoka et al.

(10) Patent No.: US 9,060,529 B2
(45) Date of Patent: Jun. 23, 2015

(54) METHOD FOR TREATMENT OF LACTO-N-BIOSE-CONTAINING SOLUTION

(75) Inventors: Motomitsu Kitaoka, Ibaraki (JP);
Mamoru Nishimoto, Ibaraki (JP);
Kanetada Shimizu, Zama (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 0 days.

(21) Appl. No.: 13/577,167

(22) PCT Filed: Jan. 31, 2011

(86) PCT No.: PCT/JP2011/051915
§ 371 (c)(1),
(2), (4) Date: Aug. 3, 2012

(87) PCT Pub. No.: WO2011/096360
PCT Pub. Date: Aug. 11, 2011

(65) Prior Publication Data
US 2012/0309708 A1    Dec. 6, 2012

(30) Foreign Application Priority Data
Feb. 5, 2010  (JP) ................... 2010-024436

(51) Int. Cl.
*A61K 31/7016* (2006.01)
*A61K 31/70* (2006.01)
*A61K 8/60* (2006.01)
*A23K 1/16* (2006.01)
*A23L 1/09* (2006.01)
*A23K 3/00* (2006.01)
*A61K 9/00* (2006.01)

(52) U.S. Cl.
CPC ............. *A23K 1/1643* (2013.01); *A23L 1/09* (2013.01); *A23V 2002/00* (2013.01); *A23K 3/00* (2013.01); *A61K 9/0095* (2013.01)

(58) Field of Classification Search
USPC ..................... 514/53; 536/123.13, 53
See application file for complete search history.

(56) References Cited

FOREIGN PATENT DOCUMENTS

| JP | 06253878 A | 9/1994 |
| JP | 2003189891 A | 7/2003 |
| JP | 2008154495 A | 7/2008 |
| JP | 2008290972 A | * 12/2008 |

OTHER PUBLICATIONS

Kitaoka et al.; JP 2008290972 A; Dec. 4, 2008 (Machine English Translation).*
Nishimoto, M. et al., "Practical preparation of lacto-N-biose I, a candidate for the bifidus factor in human milk," Bioscience, Biotechnology, and Biochemistry, Aug. 2007, vol. 71, No. 8, pp. 2101-2104.
Vetere, A. et al., "Regiospecific glycosidase-assisted synthesis of lacto-N-biose I (Galβ1-3GlcNAc) and 3'-sialyl-lacto-N-biose I (NeuAcα2-3Galβ1-3GlcNAc)," European Journal of Biochemistry, Feb. 2000, vol. 267, No. 4, pp. 942-949.
Japanese Patent Office, Office Action issued in Application No. 2011-552766, mailed Jan. 7, 2014, 6 pp.
Chiku, K. et al., "Thermal decomposition of beta-D-galactopyranosyl-(1- ->3)-2-acetamido-2-deoxy-D-hexopyranoses under neutral conditions.", Carbohydrate Research, Jun. 15, 2010, vol. 345, No. 13, pp. 1901-1908.
Chiku, K. et al., "Galβ1, 3HexNAc no Netsu Fuanteisei", Nippon Nogei Kagakukai Taikai Koen Yoshishu, Mar. 5, 2010, Lecture No. 2XAp07, vol. 2010, p. 121.
Nishimoto, M. et al., "One-pot enzymatic production of beta-D-galactopyranosyl-(1-    ->3)-2-acetamido-2-deoxy-D-galactose (galacto-N-biose) from sucrose and 2-acetamido-2-deoxy-D-galactose (N-acetylgalactosamine).", Carbohydrate Research, Oct. 1, 2009, vol. 344, No. 18, pp. 2573-2576.
International Search Report issued in International Patent Application No. PCT/JP2011/051915, mailed Apr. 19, 2011, 4 pages.
Evans, T.J. et al. "Effect of storage and heat on microbial proteins in human milk", Archives of Disease in Childhood, 1978. vol. 53, p. 239-241.
First Examination Report received in corresponding New Zealand Application No. 602203, dated Apr. 17, 2013 (2 pages).

* cited by examiner

*Primary Examiner* — Shaojia Anna Jiang
*Assistant Examiner* — Michael C Henry
(74) *Attorney, Agent, or Firm* — Wood, Herron & Evans, LLP

(57) ABSTRACT

The present invention relates to a method of treating a liquid composition containing lacto-N-biose, the method including: preparing a liquid composition containing lacto-N-biose having a pH at 25° C. of not less than 2.0 and not more than 5.5, and heating the liquid composition at a temperature of 65° C. or higher. The present invention can provide a treatment method that enables thermal decomposition of lacto-N-biose to be suppressed when a liquid composition containing lacto-N-biose is heated at a temperature of 65° C. or higher, a liquid preparation containing lacto-N-biose that is treated using the treatment method, a dried product produced from such a liquid preparation containing lacto-N-biose, and a method of producing a product containing lacto-N-biose.

4 Claims, 1 Drawing Sheet

મેthod FOR TREATMENT OF
LACTO-N-BIOSE-CONTAINING SOLUTION

TECHNICAL FIELD

The present invention relates to a method of treating a liquid composition containing lacto-N-biose, a liquid preparation containing lacto-N-biose that is treated using the treatment method and a dried product thereof, and a method of producing a product containing lacto-N-biose.

Priority is claimed on Japanese Patent Application No. 2010-024436, filed Feb. 5, 2010, the content of which is incorporated herein by reference.

BACKGROUND ART

Lacto-N-biose is a disaccharide in which galactose and N-acetylglucosamine are bonded via a β-1,3-bond (Galβ1, 3GlcNAc, hereinafter abbreviated as LNB), and is known as one of the disaccharides that constitute the oligosaccharides (milk oligosaccharides) contained in breast milk.

Conventionally, methods using microbes or enzymes have been proposed as methods of producing LNB (for example, see Patent Documents 1 to 3).

It has recently been reported that LNB has functionalities such as a *bifidobacterium* growth-promoting effect (for example, see Patent Document 4). Further, it is anticipated that LNB will also exhibit various actions that are effective in promoting and maintaining good health, such as a bowel-regulating action and an immunoregulatory action.

PRIOR ART DOCUMENTS

Patent Documents

[Patent Document 1]
Japanese Laid-Open Patent Application No. Hei 6-253878
[Patent Document 2]
Japanese Laid-Open Patent Application No. 2003-189891
[Patent Document 3]
Japanese Laid-Open Patent Application No. 2008-154495
[Patent Document 4]
Japanese Laid-Open Patent Application No. 2008-290972

DISCLOSURE OF INVENTION

Problems to be Solved by the Invention

Accordingly, the addition of LNB to various types of products including food, pharmaceutical, cosmetics and feed can be considered.

When LNB is added to these products, a heat treatment at a temperature of 65° C. or higher is required for the purposes of sterilization or the like, either on the LNB prior to addition, or on the product containing the added LNB.

However, according to investigations conducted by the inventors of the present invention, when this type of heat treatment is performed on a liquid composition containing LNB, the LNB within the liquid composition may suffer various problems, including decomposition, denaturation, and loss of bioactivity. Accordingly, in the case of a product that includes a heat treatment within the production process, it is expected that a sufficient heat treatment will be unable to be performed during production.

The present invention has been developed in light of these circumstances, and has an object of providing a treatment method that enables thermal decomposition of LNB to be suppressed when an liquid composition containing LNB is heated at a temperature of 65° C. or higher, as well as providing a liquid preparation containing LNB that is treated using the treatment method, a dried product produced from such an liquid preparation containing LNB, and a method of producing a product containing LNB.

Means to Solve the Problems

As a result of intensive investigation, the inventors of the present invention discovered that when a liquid composition containing LNB is heated at a temperature of 65° C. or higher, a dehydrate of N-acetylglucosamine (GlcNAc) and galactose (Gal) are produced as decomposed or denatured products. Based on this finding, the inventors conducted further research of the thermal decomposition reaction using these decomposed or denatured products as indicators, and discovered that the LNB within a liquid composition containing LNB exhibits low thermal stability and undergoes rapid thermal decomposition under neutral or alkaline conditions, but when the pH is within a range from not more than 5.5 to not less than 2.0, the progress of the thermal decomposition reaction is inhibited, and they were therefore able to complete the present invention.

In order to achieve the object described above, the present invention adopts the aspects described below.

<1> A method of treating a liquid composition containing LNB, the method including: preparing a liquid composition containing LNB having a pH at 25° C. of not less than 2.0 and not more than 5.5, and heating the liquid composition at a temperature of 65° C. or higher.

<2> The method according to <1>, wherein the liquid composition containing LNB is a food, pharmaceutical, cosmetics or feed, which is in liquid form.

<3> A liquid preparation containing LNB that is treated using the method according to <1> or <2>.

<4> A dried product of a liquid preparation containing LNB that is treated using the method according to <1> or <2>.

<5> A method of producing a product containing LNB, the method including adding a liquid preparation containing LNB that is treated using the method according to <1> or <2> or a dried product thereof to a food, pharmaceutical, cosmetics, or feed.

Effect of the Invention

The present invention is able to provide a treatment method that enables thermal decomposition of LNB to be suppressed when a liquid composition containing LNB is heated at a temperature of 65° C. or higher, a liquid preparation containing LNB that is treated using the treatment method, a dried product produced from such a liquid preparation containing LNB, and a method of producing a product containing LNB.

BEST MODE FOR CARRYING OUT THE INVENTION

Figure 1:
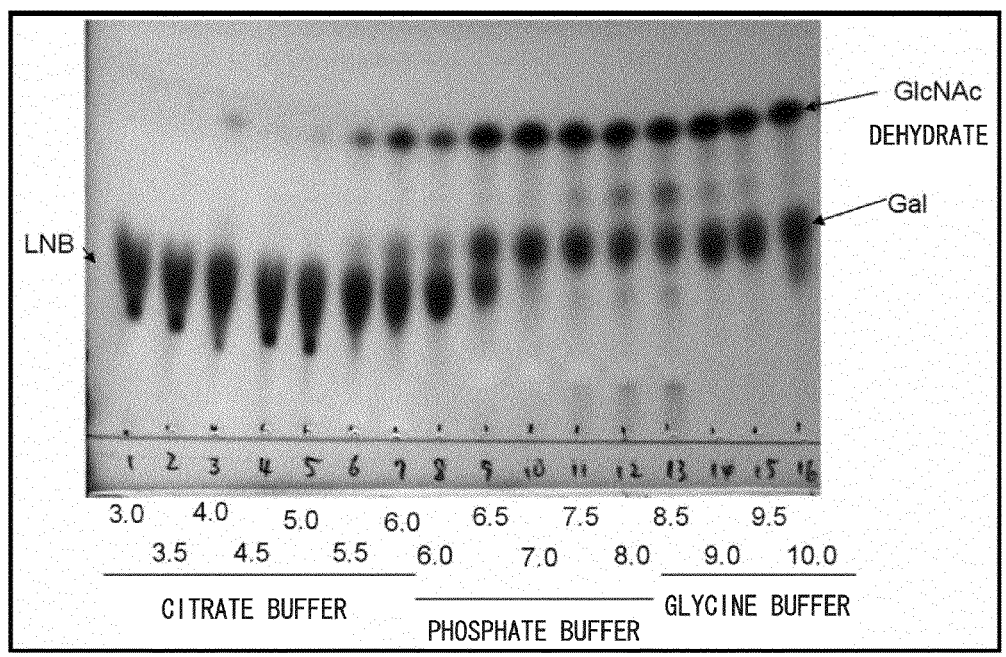
FIG. 1 is a photograph illustrating the results of a test example 1 (showing the TLC detection patterns following heat treatment at 90° C. for 60 minutes for liquid compositions containing LNB of different pH).

In the treatment method of the present invention, first, a liquid composition containing LNB having a pH at 25° C. of not less than 2.0 and not more than 5.5 is prepared. The pH is preferably not less than 2.0 and not more than 5.0, and still more preferably not less than 2.0 and not more than 4.5. If the pH of the liquid composition containing LNB is greater than 5.5 or less than 2.0, then when heat treatment is performed at a temperature of 65° C. or higher in the following step, decomposition of the LNB tends to occur more readily, and if the pH exceeds 7.0, then the LNB tends to undergo complete decomposition. It is thought that when the pH is less than 2.0, acid decomposition occurs in addition to thermal decomposition. Provided the pH of the liquid composition containing LNB is within the range from not less than 2.0 to not more than 5.0, decomposition of the LNB is not likely to undergo decomposition when heat treatment is performed at a temperature of 65° C. or higher in the following step.

In the present invention, a "liquid composition containing LNB having a pH at 25° C. of not less than 2.0 and not more than 5.5" describes a liquid composition containing LNB for which the pH satisfies the above range at a standard temperature of 25° C. In other words, when the temperature of the liquid composition containing LNB is altered to a temperature other than 25° C., the pH range will be adjusted in accordance with the temperature. Preparation of a liquid composition containing LNB having this type of adjusted pH range is also included within the scope of the present invention.

In other words, preparation of a liquid composition containing LNB for which the pH at an arbitrary temperature does not fall within the range from not less than 2.0 to not more than 5.5 is still included within the scope of the present invention provided the pH satisfies the range from not less than 2.0 to not more than 5.5 when the temperature is altered to the standard temperature of 25° C.

For example, a liquid composition containing LNB having a pH of 1.90 at a temperature of 65° C. has a pH of 2.01 when the temperature is adjusted to the standard temperature of 25° C., and therefore preparation of this liquid composition containing LNB followed by heat treatment at a temperature of 65° C. or higher in the subsequent step is included within the scope of the present invention.

Examples of the liquid composition containing LNB include solutions prepared by dissolving LNB in a solvent such as water (hereinafter referred to as "LNB solutions"), liquid compounds obtained by adding LNB or an LNB solution to a liquid product (such as food, pharmaceutical, cosmetics or feed, which is in liquid form) (hereinafter referred to as "LNB-added liquid products"), and liquid products (such as food, pharmaceutical, cosmetics or feed, which is in liquid form) that naturally contain LNB as a component (hereinafter referred to as "liquid products containing natural LNB").

There are no particular limitations on the method used for preparing the liquid composition containing LNB having a pH of not less than 2.0 and not more than 5.5, and examples include the methods (1) and (2) described below.

(1) A method in which the pH of a liquid composition containing LNB having a pH exceeding 5.5 (hereinafter referred to as a "high-pH liquid composition containing LNB") is adjusted to a value of not less than 2.0 and not more than 5.5.

(2) A method of dissolving LNB in a liquid composition having a pH of not less than 2.0 and not more than 5.5.

In method (1), the high-pH liquid composition containing LNB may be any one of the above-mentioned LNB solutions, LNB-added liquid products or liquid products containing natural LNB.

The pH of the high-pH liquid composition containing LNB can be adjusted by adding an acid. The acid may be selected appropriately from those acids conventionally used for pH adjustment, and a single acid or a combination of two or more acids may be selected from among inorganic acids such as hydrochloric acid and phosphoric acid, and organic acids such as citric acid and acetic acid.

Examples of the liquid composition having a pH of not less than 2.0 and not more than 5.5 used in the method (2) include liquids in which the pH of a liquid having a pH exceeding 5.5 (such as water or a buffer solution) has been adjusted using the same method as that described for the method (1), and liquid products having a pH of not less than 2.0 and not more than 5.5 (such as the fruit juice of citrus fruits such as oranges).

There are no particular limitations on the method used for producing the LNB, which may be selected appropriately from conventional methods. Examples include a method in which a substrate containing lactose and N-acetylglucosamine is used as a starting material, and this starting material is reacted sequentially with β-galactosidase sourced from porcine testes and β-galactosidase produced by *Bacillus circulans* (see Japanese Laid-Open Patent Application No. Hei 06-253878), a method that uses microbes, animal cells or insect cells capable of producing a complex carbohydrate from a sugar nucleotide and a complex carbohydrate precursor (see Japanese Laid-Open Patent Application No. 2003-189891), and an LNB production method based on an enzymatic method (see Japanese Laid-Open Patent Application No. 2008-154495). Among these methods, the method described below and disclosed in Japanese Laid-Open Patent Application No. 2008-154495 is preferred in terms of offering superior simplicity.

Namely, a method in which:

(i) a combination of a carbohydrate raw material and an enzyme that produces α-glucose-1-phosphate by phosphorolysis of the carbohydrate raw material, and (ii) a combination of an enzyme that converts α-glucose-1-phosphate to UDP-glucose, an enzyme that converts UDP-galactose to galactose-1-phosphate, and their cofactors, and/or a combination of an enzyme (UDP-Gly production enzyme) that converts α-glucose-1-phosphate and UDP-galactose to UDP-glucose and α-galactose-1-phosphate respectively and its cofactor are reacted in the presence of N-acetylglucosamine, phosphoric acid, LNB phosphorylase (EC 2.4.1.211) and UDP-glucose-4-epimerase (EC 5.1.3.2). The LNB synthesis reaction using microbes or enzymes mentioned above is typically performed in a liquid having a pH of approximately 7.0 to 7.5, and the reaction temperature is set to approximately 37° C. The LNB contained within the obtained reaction liquid composition can be recovered using conventional methods such as column chromatography.

The heat treatment of the liquid composition containing LNB having a pH of not less than 2.0 and not more than 5.5 is performed at a temperature of 65° C. or higher.

In order to ensure sufficient suppression of thermal decomposition of the LNB, the upper limit for the heat treatment temperature is typically not more than 140° C.

A preferred heat treatment temperature may be set appropriately within the above range in accordance with the intended purpose of the heat treatment. For example, when heat sterilization is the main purpose, the heat treatment temperature is preferably within a range from 65 to 140° C., and more preferably from 80 to 140° C.

Further, in cases during food processing or the like where the purpose of the heat treatment is not heat sterilization (for example, heat treatment for a purpose such as protein denaturation), the heat treatment temperature is preferably within a range from 70 to 120° C., and more preferably from 80 to 100° C.

The heating time varies depending on the heat treatment temperature, but is typically within a range from 2 seconds to 60 minutes, and preferably from 2 seconds to 10 minutes.

Following cooling by conventional methods, the heated liquid preparation containing LNB may, if required, be sealed inside a container to produce a container-packaged liquid product containing LNB.

The heated liquid preparation containing LNB may also be dried to produce a dried product. For example, a liquid preparation containing LNB prepared by heat treatment an LNB solution containing only LNB using the heat treatment of the present invention may be dried to produce LNB powder. Freeze drying is preferred as the method of drying the liquid preparation containing LNB as it ensures excellent stability of the LNB.

The heated liquid preparation containing LNB obtained in the manner described above or the dried product thereof either contains no LNB decomposed or denatured products, or contains very little of such products.

According to the treatment method of the present invention, a liquid composition containing LNB that contains LNB, which is expected to exhibit various types of bioactivity, can be heated for the purpose of heat sterilization or some other processing purpose, with no loss in the bioactivity.

As a result, the treatment method of the present invention can be applied to any process and treatment that includes a heat treatment step at the time of production of various products such as food, pharmaceutical, cosmetics and feed.

For example, by using a liquid product (such as a food, pharmaceutical, cosmetics or feed, which is in liquid form) as the liquid composition containing LNB that is subjected to the heat treatment, a heated product containing LNB (such as a food containing LNB, pharmaceutical containing LNB, cosmetics containing LNB or feed containing LNB) can be obtained with no loss in the LNB activity.

Further, by adding a liquid preparation containing LNB which is heated in the manner described above or a dried product thereof to any of various products (such as food, pharmaceutical, cosmetics or feed), an product containing LNB can be produced.

Moreover, because the LNB contained within the liquid preparation containing LNB or dried product thereof obtained using the treatment method of the present invention is one of the disaccharides that constitute the naturally occurring oligosaccharides (milk oligosaccharides) in breast milk, addition of the LNB to food, pharmaceutical and cosmetics and the like is safe.

EXAMPLES

The present invention is described in more detail below using a series of test examples and examples, but the present invention is in no way limited by the following examples.

In the examples presented below, all pH values refer to the pH value at 25° C., and were measured using a Horiba Navi F-25 (manufactured by Horiba, Ltd.).

Production Example 1

Preparation of LNB Powder

According to the LNB production method using an enzymatic method disclosed in Japanese Laid-Open Patent Application No. 2008-154495, an LNB powder was prepared using the procedure described below.

Reaction was performed in accordance with the description of Example 8 in Japanese Laid-Open Patent Application No. 2008-154495, yielding a reaction liquid composition with an LNB concentration of 50 mM.

Following demineralization, the obtained reaction liquid composition was supplied to a chromatography column filled with Toyopearl HW40F (manufactured by Tosoh Corporation) as a filler, and the disaccharide fraction was isolated and freeze dried, yielding 1 kg of an LNB powder having a purity of 95%.

Test Example 1

The purpose of this test was to evaluate the effect of the pH of a liquid composition containing LNB on the stability of the LNB upon heating.
1) Test Method:

Samples of the LNB powder prepared in the above Production Example 1 were dissolved at a concentration of 2% (by mass, this also applies to all subsequent concentration values) in a 0.1 M citrate buffer solution (pH: 3.0 to 6.0), a 0.1 M phosphate buffer solution (pH: 6.0 to 8.0) or a 0.1 M glycine buffer solution (pH: 8.5 to 10.5), thus preparing samples (liquid compositions containing LNB) 1 to 16 having pH values at intervals of 0.5 across the entire pH range mentioned above.

A 5 mL sample of each of the prepared samples 1 to 16 was dispensed into a test tube and heated at 90° C. for 60 minutes.

Each of the heated samples was cooled to 15° C., and 1 μL was then spotted onto a silica gel thin layer chromatography (TLC) plate. The plate was developed using an 80% acetonitrile solvent, and was then immersed in a 5% sulfuric acid solution and colorized by heating in an oven. The existence or absence of decomposed or denatured products (N-acetylglucosamine dehydrate and galactose) and the amount of those decomposed or denatured products were evaluated visually to determine whether or not decomposition had occurred, and if so, the extent of that decomposition.
2) Test Results:

The test results are shown in FIG. 1. FIG. 1 is a photograph showing the TLC detection pattern for each of the samples of differing pH following heat treatment at 90° C. for 60 minutes. In FIG. 1, Gal represents galactose and GlcNAc represents N-acetylglucosamine.

As is evident from FIG. 1, under the heat treatment conditions described above, the LNB was stable and underwent almost no decomposition when the pH was 5.5 or less, and particularly 5.0 or less. In contrast, when the pH was 6.0 or higher, and particularly 7.0 or higher, significant amounts of decomposed or denatured products were observed, indicating that the LNB was unstable.

Test Example 2

The purpose of this test was to evaluate the effect of the heating temperature and time on the stability of LNB within a neutral liquid composition containing LNB.

1) Test Method:

The LNB powder prepared in the above Production Example 1 was dissolved at a concentration of 2% in a 0.1 M phosphate buffer of pH 7.0 to prepare a sample (liquid composition containing LNB).

5 mL samples of the prepared sample were dispensed into test tubes, which were heated at 90° C. for 0, 10, 20, 30, 40, 50 or 60 minutes, or heated at 65, 67, 70, 75, 80, 85 or 88° C. for 60 minutes.

Each of the heated samples was cooled to 15° C., and the same method as that described for Test Example 1 was used to determine whether or not decomposition had occurred, and if so, the extent of that decomposition.

Figure 2:
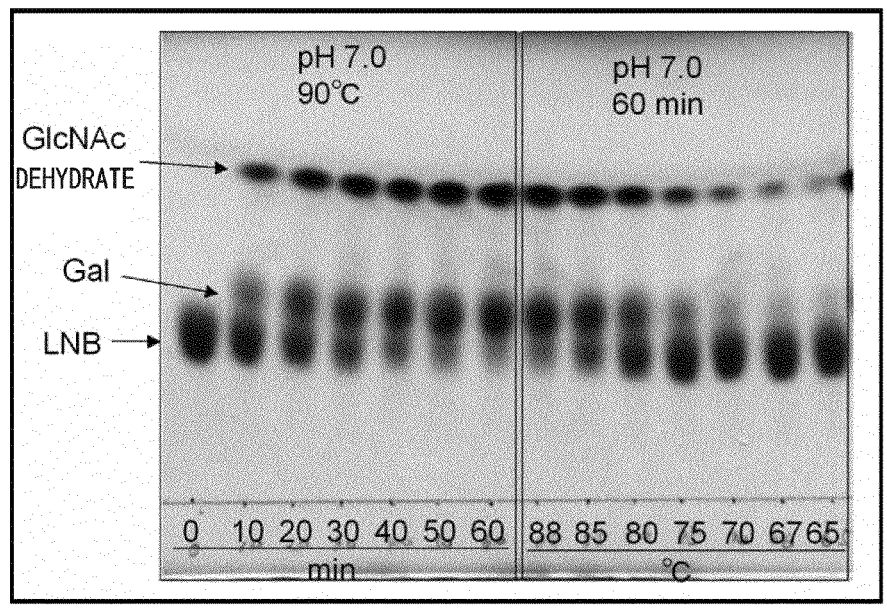
FIG. 2 is a photograph illustrating the results of a test example 2 (showing the TLC detection patterns following heat treatment at different temperatures and different time periods for a liquid composition containing LNB having a pH of 7.0).

2) Test Results:

The test results are shown in FIG. 2. FIG. 2 is a photograph showing the TLC detection pattern for each of the liquid compositions containing LNB at pH 7.0 following heat treatment at different temperatures and for different time periods.

As is evident from FIG. 2, decomposed or denatured products were detected under all of the different heat treatment conditions, and the amounts of those decomposition products increased as the heating time was lengthened, and as the heating temperature was increased. These results confirmed that LNB decomposed under any heating conditions at a neutral range, and the extent of that decomposition was directly proportional to the heating time and the temperature.

Test Example 3

The purpose of this test was to evaluate the effect of the heating temperature and time on the stability of LNB within liquid compositions containing LNB having a pH of 5.5 or lower.

1) Test Method:

Samples of the LNB powder prepared in the above Production Example 1 were dissolved at a concentration of 2% in a 0.1 M citrate buffer solution (pH: 5.5, 5.0, 4.0, 3.0) to prepare a series of liquid compositions containing LNB. Further, a portion of the LNB solution having a pH of 3.0 was used to prepare solutions having a pH of 2.0 or 1.0 by adding 1 M hydrochloric acid.

In a separate preparation, a sample of the LNB powder was dissolved at a concentration of 2% in a 0.1 M phosphate buffer having a pH of 7.0 to prepare a liquid composition containing LNB.

Sets containing the liquid compositions containing LNB at each pH value were each heated at a predetermined temperature (65, 70, 80, 90, 100 or 120° C.) for a predetermined period of time (5, 10, 20, 30 or 60 minutes).

Each of the heated liquid compositions containing LNB was cooled, and the same method as that described for Test Example 1 was used to determine whether or not decomposition had occurred, and if so, the extent of that decomposition. Based on the results, the extent of decomposition was evaluated against the criteria listed below.

(Evaluation Criteria)
− no decomposition
± slight decomposition
+ partial decomposition
++ majority decomposition
+++ almost total decomposition 2) Test Results:

The test results are shown in Table 1.

As is evident from Table 1, within the pH range from not less than 2.0 to not more than 5.5, the LNB was stable and underwent almost no decomposition. This effect was particularly superior for pH values of not less than 2.0 and not more than 5.0, and even more superior for pH values of not less than 2.0 and not more than 4.0. In contrast, in the case of the liquid compositions containing LNB having a pH of 7.0 or 1.0, decomposition occurred even after heating for 5 minutes, and the extent of that decomposition was directly proportional to the heating time and the temperature.

TABLE 1

| pH | Heating temperature (° C.) | Heating time (minutes) | | | | |
|---|---|---|---|---|---|---|
| | | 5 | 10 | 20 | 30 | 60 |
| 7.0 | 65 | − | − | − | ± | + |
| | 70 | − | − | ± | + | + |
| | 80 | − | ± | + | + | ++ |
| | 90 | ± | + | ++ | ++ | +++ |
| | 100 | + | + | ++ | ++ | +++ |
| | 120 | ++ | +++ | +++ | +++ | +++ |
| 5.5 | 65 | − | − | − | − | − |
| | 70 | − | − | − | − | − |
| | 80 | − | − | − | − | − |
| | 90 | − | − | − | − | ± |
| | 100 | − | − | − | ± | + |
| | 120 | − | ± | + | + | + |
| 5.0 | 65 | − | − | − | − | − |
| | 70 | − | − | − | − | − |
| | 80 | − | − | − | − | − |
| | 90 | − | − | − | − | − |
| | 100 | − | − | − | − | ± |
| | 120 | − | − | ± | ± | ± |
| 4.0 | 65 | − | − | − | − | − |
| | 70 | − | − | − | − | − |
| | 80 | − | − | − | − | − |
| | 90 | − | − | − | − | − |
| | 100 | − | − | − | − | − |
| | 120 | − | − | − | − | − |
| 3.0 | 65 | − | − | − | − | − |
| | 70 | − | − | − | − | − |
| | 80 | − | − | − | − | − |
| | 90 | − | − | − | − | − |
| | 100 | − | − | − | − | − |
| | 120 | − | − | − | − | − |
| 2.0 | 65 | − | − | − | − | − |
| | 70 | − | − | − | − | − |
| | 80 | − | − | − | − | − |
| | 90 | − | − | − | − | − |
| | 100 | − | − | − | − | − |
| | 120 | − | − | − | − | ± |
| 1.0 | 65 | − | − | − | − | − |
| | 70 | − | − | − | − | − |
| | 80 | − | − | − | ± | + |
| | 90 | − | ± | ± | + | ++ |
| | 100 | ± | ± | + | ++ | ++ |
| | 120 | ++ | ++ | +++ | +++ | +++ |

Example 1

100 g of the LNB powder prepared in the above Production Example 1 was dissolved in 9.9 kg of purified water, and 0.1 M hydrochloric acid was added to the solution to adjust the pH to 4.5. The resulting aqueous solution was preheated for 3 minutes at 70° C. using a UHT sterilizer (manufactured by Morinaga Engineering Co., Ltd.), subsequently sterilized at 130° C. for 2 seconds, and then cooled to 15° C., yielding 10 kg of a liquid preparation containing LNB.

This liquid preparation containing LNB was analyzed using the same TLC method as that described for Test Example 1, and the results confirmed that the LNB had not decomposed.

Example 2

100 g of the LNB powder prepared in the above Production Example 1 was added to 9.9 kg of a commercially available orange juice (manufactured by Morinaga Milk Industry Co., Ltd.), and the resulting mixture was heated at 80° C. for 15 minutes and then cooled to 15° C. 100 mL aliquots of the juice were used to fill glass bottles, which were then sealed, yielding 100 bottles of orange juice containing LNB.

The pH of the obtained orange juice was 4.51, and analysis of the orange juice using the same TLC method as that described for Test Example 1 confirmed that the LNB had not decomposed.

Example 3

100 g of the LNB powder prepared in the above Production Example 1 was dissolved in 9.9 kg of purified water, and 0.1 M citric acid was added to the solution to adjust the pH to 5.0. The resulting aqueous solution was heated at 90° C. for 30 minutes, and then cooled to 15° C., yielding 10 kg of a liquid preparation containing LNB.

This liquid preparation containing LNB (heated liquid composition) was analyzed using the same TLC method as that described for Test Example 1, and the results confirmed that the LNB had not decomposed.

Freeze drying the heated liquid preparation yielded 100 g of powder.

Example 4

10 g of the powder (heated LNB powder) obtained in Example 3 was added to a formulation of the components listed in the table below, and ion-exchanged water was added to bring the total volume to 300 mL, thus preparing a liquid preparation for oral administration containing lacto-N-biose. In Table 2, the "appropriate amount" of the citrate buffer is an amount sufficient to adjust the pH to 5.0.

TABLE 2

| | |
|---|---|
| Dried carrot extract | 214 mg |
| Dried *epimedium grandiflorum* extract | 50 mg |
| Ursodesoxycholic acid | 25 mg |
| D-sorbitol | 50 g |
| Sucrose | 25 g |
| Polyoxyethylene hardened castor oil | 3 g |
| Propylene glycol | 5 mL |
| Sodium benzoate | 600 mg |
| Butyl paraoxybenzoate | 10 mg |
| Citrate buffer | appropriate amount |

INDUSTRIAL APPLICABILITY

The present invention is able to provide a treatment method that enables thermal decomposition of LNB to be suppressed when a liquid composition containing LNB is heated at a temperature of 65° C. or higher, a liquid preparation containing LNB that is treated using the treatment method, a dried product produced from such a liquid preparation containing LNB, and a method of producing a product containing LNB, and is therefore useful in the production of food, pharmaceutical, cosmetics and feed and the like.

The invention claimed is:

1. A method of producing a heated liquid preparation containing lacto-N-biose, the method comprising:
   preparing a liquid composition containing lacto-N-biose by
   (A) adding an acid to an aqueous solvent to adjust the pH at 25° C. to not less than 2.0 and not more than 5.0, followed by dissolving lacto-N-biose in the solvent to prepare the liquid composition, or
   (B) dissolving lacto-N-biose in an aqueous solvent, followed by adding an acid to the solvent in which lacto-N-biose has been dissolved to adjust the pH at 25° C. to not less than 2.0 and not more than 5.0 to prepare the liquid composition; and
   heating the liquid composition at a temperature of not less than 65° C. and not more than 140° C.

2. A method of producing a product containing heated lacto-N-biose, the method comprising:
   producing a heated liquid preparation containing lacto-N-biose by the method according to claim 1, and
   mixing the heated liquid preparation and a product selected from the group consisting of a food, pharmaceutical, cosmetics, and feed.

3. A method of producing a dried product containing heated lacto-N-biose, the method comprising:
   producing a heated liquid preparation containing lacto-N-biose by the method according to claim 1, and
   drying the heated liquid preparation.

4. The method of claim 3 further comprising mixing the dried heated liquid preparation and a product selected from the group consisting of a food, pharmaceutical, cosmetics, and feed.

* * * * *